(12) United States Patent
Zheng et al.

(10) Patent No.: US 11,596,930 B2
(45) Date of Patent: Mar. 7, 2023

(54) NICKEL/TITANIUM OXIDE-SILICON OXIDE CATALYST FOR SYNTHESIZING TERPINENE-4-OL, PREPARATION METHOD THEREOF, AND METHOD OF SYNTHESIZING TERPINENE-4-OL USING THE SAME

(71) Applicant: Fuzhou University, Fuzhou (CN)

(72) Inventors: Huidong Zheng, Fuzhou (CN); Dan Wu, Fuzhou (CN); Jingjing Chen, Fuzhou (CN); Jie Liu, Fuzhou (CN); Naixin Wu, Fuzhou (CN)

(73) Assignee: Fuzhou University, Fuzhou (CN)

( * ) Notice: Subject to any disclaimer, the term of this patent is extended or adjusted under 35 U.S.C. 154(b) by 93 days.

(21) Appl. No.: 17/225,138

(22) Filed: Apr. 8, 2021

(65) Prior Publication Data

US 2021/0316280 A1 Oct. 14, 2021

(30) Foreign Application Priority Data

Apr. 8, 2020 (CN) .......................... 202010270837.3

(51) Int. Cl.
*B01J 23/755* (2006.01)
*B01J 21/08* (2006.01)
(Continued)

(52) U.S. Cl.
CPC ............. *B01J 23/755* (2013.01); *B01J 21/08* (2013.01); *B01J 37/009* (2013.01); *B01J 37/04* (2013.01); *B01J 37/06* (2013.01); *B01J 37/082* (2013.01); *B01J 37/18* (2013.01); *C07C 29/132* (2013.01); *C07C 29/84* (2013.01); *B01J 2231/52* (2013.01); *B01J 2231/645* (2013.01)

(58) Field of Classification Search
CPC ....... C07C 29/132; C07C 29/84; C07C 35/18; C07C 29/80; C07C 29/76; C07C 29/56; B01J 23/755; B01J 21/08; B01J 2231/52; B01J 2231/645
See application file for complete search history.

(56) References Cited

U.S. PATENT DOCUMENTS 10,266,468 B2 * 4/2019 Wolf ....................... C07C 29/56

* cited by examiner

*Primary Examiner* — Jafar F Parsa

(57) ABSTRACT

The present invention discloses a nickel/titanium oxide-silicon oxide catalyst for synthesizing terpinene-4-ol as well as a preparation method and method of synthesizing terpinene-4-ol using the same. The preparation method includes the steps of catalyst preparation, terpinene-4-ol synthesis and the like are disclosed in the present invention. The preparation method includes the following steps: firstly, preparing a mixed colloid of $TiO_2$ and $SiO_2$ by using a sol-gel method, and then centrifuging, washing, drying and roasting is performed to prepare a $TiO_2$—$SiO_2$ binary oxide; then, preparing Ni/TiO2-SiO2 by dipping in a nickel nitrate solution, and preparing a supported catalyst by drying and roasting; and finally, adopting a terpinolene-4, 8-epoxide a raw material, carrying out isomerization under the dual catalytic action of TiO2-SiO2 and Ni of the supported catalyst, and carrying out hydrogenation to prepare terpinene-4-ol. The preparation method can combine isomerization and hydrogenation reaction on the same catalyst, has good selectivity on terpinene-4-ol, and is simple to operate and high in product yield.

4 Claims, 3 Drawing Sheets

(51) Int. Cl.
*B01J 37/00* (2006.01)
*B01J 37/04* (2006.01)
*B01J 37/06* (2006.01)
*B01J 37/08* (2006.01)
*B01J 37/18* (2006.01)
*C07C 29/132* (2006.01)
*C07C 29/84* (2006.01)

NICKEL/TITANIUM OXIDE-SILICON OXIDE CATALYST FOR SYNTHESIZING TERPINENE-4-OL, PREPARATION METHOD THEREOF, AND METHOD OF SYNTHESIZING TERPINENE-4-OL USING THE SAME

BACKGROUND OF THE INVENTION

1. Field of the Invention

The invention relates to a chemical synthesis, and specifically relates to a nickel/titanium oxide-silicon oxide catalyst for synthesizing terpinen-4-ol, and a preparation method and method of synthesizing terpinen-4-ol using the same.

2. Description of the Prior Art

Terpinen-4-ol, also called 4-terpineol, is a kind of monocyclic monoterpene alcohol, a colorless oily liquid, with a warm peppery fragrance, a lighter earthy fragrance and a lily fragrance. It is an important fine Chemical products and can be used to prepare advanced flavors and fragrances and as pharmaceutical intermediates to treat various skin diseases such as blepharitis, red eye, and dry eye. It has broad-spectrum antimicrobial, antibacterial, anti-inflammatory, analgesic, mild fragrance and non-corrosive. The advantages thereof are ideal disinfectants, preservatives and spices.

At present, there are two main methods for artificially synthesizing terpinen-4-ol. One method uses 1,4-cineole as a raw material to obtain terpinen-4-ol through catalytic ring opening, which is the simplest and most efficient. However, it is restricted by the scarcity of 1,4-cineole resources. The other method is using terpinolene, one of the components of turpentine, as the raw material to obtain terpinen-4-ol after partial epoxidation or photosensitive oxidation followed by hydrogenation reduction. The current problems of terpinen-4-ol produced by reduction are the poor catalytic performance of the catalyst and the difficulty of recovery.

SUMMARY OF THE INVENTION

The purpose of the present invention is to provide a sol-gel method and an impregnation method to prepare an isomerization and hydrogenation dual-functional catalyst $Ni/TiO_2$—$SiO_2$. The catalyst has simple process, no pollution, can be reused, and is used for isopine. The oleyl epoxide is isomerized and hydrogenated to prepare terpinen-4-ol with a conversion rate of 99% and a selectivity of 70%.

In order to achieve the above objective, the technical scheme of the present invention is as follows:

A preparation method of $Ni/TiO_2$—$SiO_2$ catalyst for the synthesis of terpinen-4-ol, including the following steps:

(1) Tetraethyl silicate is added to the mixed solution of ethanol, water and alkali twice, and hydrolyzed at 20-50° C. 1-6 h to get $SiO_2$ emulsion;

In some embodiment, the alkali in step (1) is ammonia;

(2) $SiO_2$ emulsion is re-dispersed in a mixed solution of ethanol, water and acid after centrifugation and wash;

In some embodiment, the acid in step (2) is hydrochloric acid;

(3) Tetrabutyl titanate is added dropwise to the above solution, and hydrolyzed at 50-100° C. for 2-8 h to obtain $TiO_2$—$SiO_2$ binary oxide emulsion;

In some embodiment, the ratio of the molar amount of tetrabutyl titanate to the molar amount of tetraethyl silicate added in step (3) is 0.2-1.2;

(4) The binary oxide emulsion is centrifuged, washed, dried and roasted at 300-700° C. for 2-8 hours to obtain solid $TiO_2$—$SiO_2$ binary oxide;

In some embodiment, the roasting temperature in step (4) is 300-500° C.;

(5) The solid $TiO_2$—$SiO_2$ binary oxide is added to the nickel nitrate solution for immersion and stirred overnight;

In some embodiment, the concentration of the nickel nitrate solution in step (5) is 0.1-1 mol/L;

(6) Dry at 70-110° C., roast at 300-700° C. for 2-8 h;

In some embodiment, the roasting time in step (6) is 3-6 h;

(7) The $Ni/TiO_2$—$SiO_2$ catalyst can be obtained by reducing under hydrogen flow; In some embodiment, the reduction temperature in step (7) is 300-700° C.;

The $Ni/TiO_2$—$SiO_2$ catalyst obtained in the present invention can be used or applied to synthesize terpinen-4-ol, including the following steps;

(1) Terpinolene epoxide and $Ni/TiO_2$—$SiO_2$ catalyst is added into the tank reactor, mixed and stirred evenly, the temperature is slowly raised to a certain temperature for isomerization reaction; after the isomerization and cooling to another certain temperature, hydrogen gas is introduced for hydrogenation reaction;

In some embodiment, the isomerization reaction temperature in step (1) is 120-150° C.;

In some embodiment, the isomerization reaction time in step (1) is 12-20 h;

In some embodiment, the hydrogenation reaction temperature in step (1) is 60-90° C.;

2) After the hydrogenation reaction is completed, the solution after the reaction is centrifuged to recover the catalyst, and the filtrate is subjected to vacuum distillation to obtain high-purity terpinen-4-ol.

The invention has the following advantages:

(1) The preparation of the catalyst is simple, pollution-free, and the catalyst is easy to recycle;

(2) It can combine isomerization and hydrogenation reaction on one catalyst, avoiding the situation that there are many by-products of hydrogenation in one step;

(3) The requirements for raw materials are low, and the yield is high, the conversion rate reaches 99%, and the selectivity reaches 65%.

DETAILED DESCRIPTION OF THE INVENTION

Figure 1:
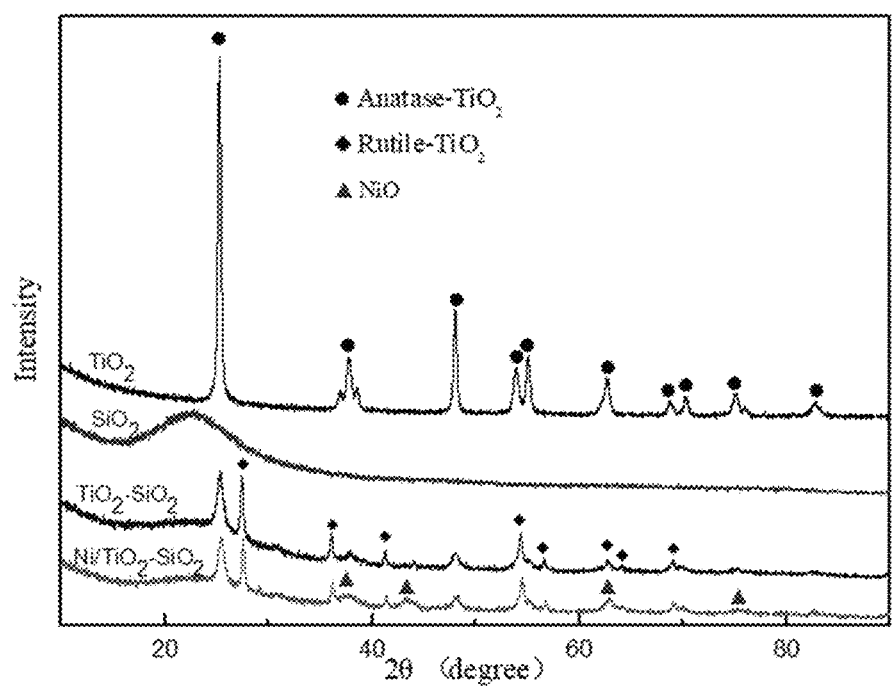
FIG. 1 is the XRD pattern of $TiO_2$, $SiO_2$, $TiO_2$—$SiO_2$, $Ni/TiO_2$—$SiO_2$ catalyst.
Figure 2:
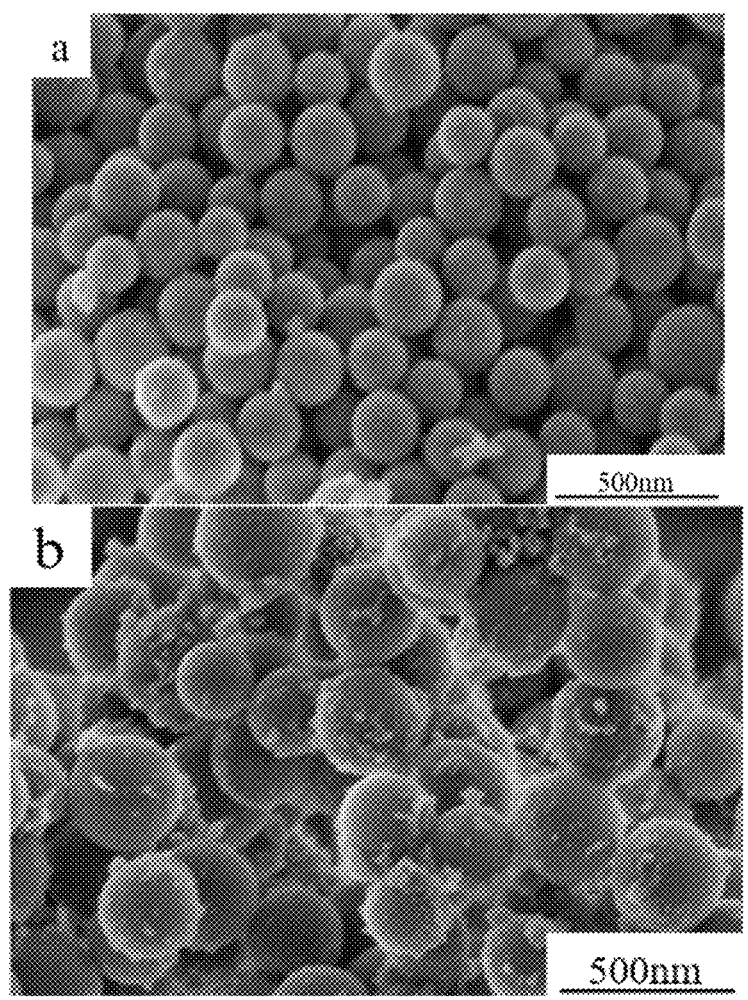
FIG. 2 is the SEM image of $TiO_2$—$SiO_2$ (a) and $Ni/TiO_2$—$SiO_2$ (b) catalysts.
Figure 3:
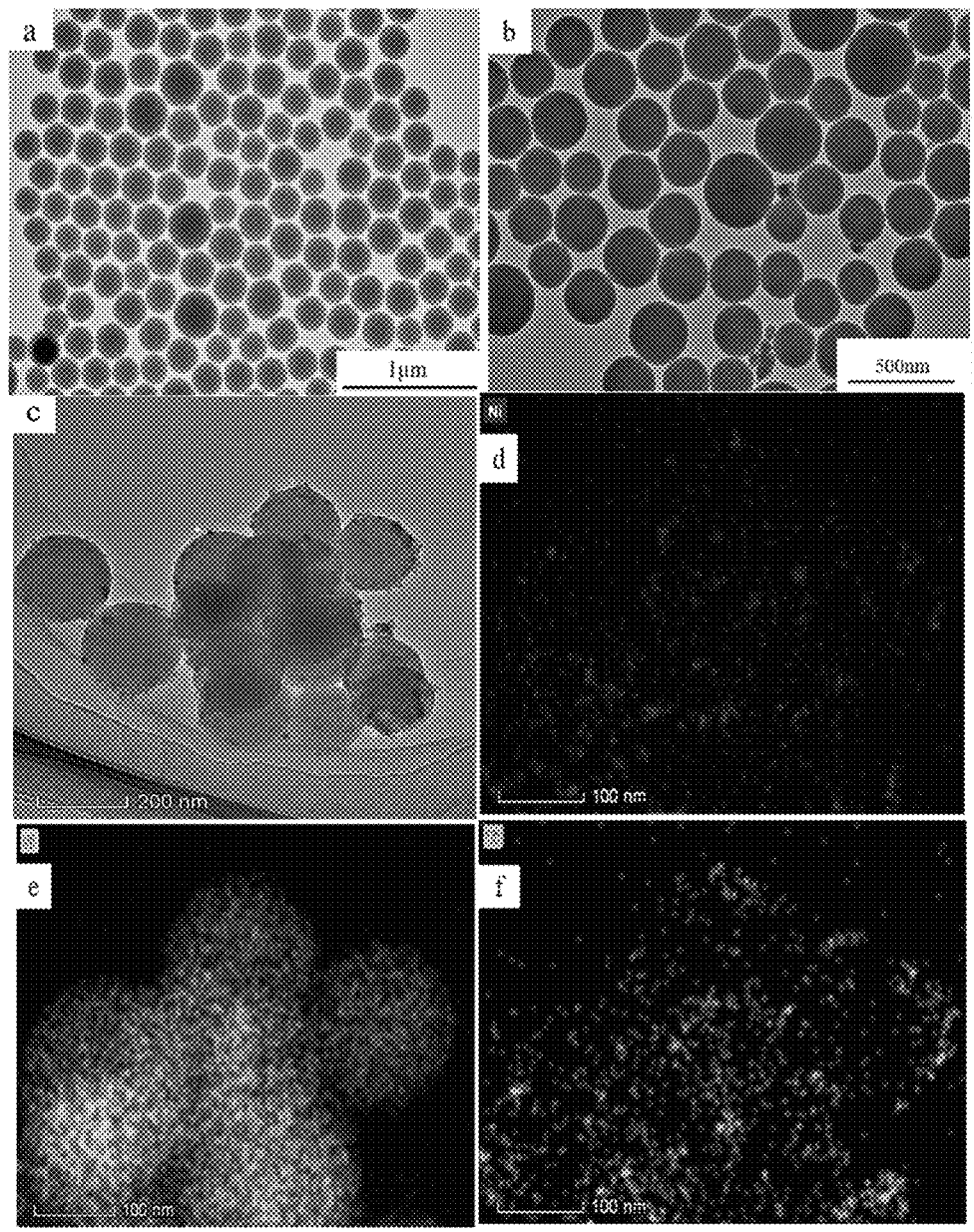
FIG. 3 shows the TEM images of $SiO_2$ (a), $TiO_2$—$SiO_2$ (b), $Ni/TiO_2$—$SiO_2$ (c) and the element mapping of Ni (d), Si (e) and Ti (f).

To describe the technical contents, the structural features, the achieved objective and effect in detail, the following id described in detail with reference to the specific embodiments and the accompanying drawings.

Embodiment 1

Step 1: Ethanol, water and ammonia solution is set and the pH of the solution is adjusted to about 11.6. 6 mL of tetraethyl silicate is slowly added dropwise to the mixed solution and the solution is heat to 40° C. and stirred for 3 h to prepare $SiO_2$ emulsion. The $SiO_2$ emulsion is centrifuged and washed, and then redispersed evenly into a mixed solution of ethanol, water and hydrochloric acid. The pH of the solution is adjusted to about 1.5 and 5 mL of tetrabutyl titanate is slowly added dropwise to the mixed solution of step 2, and the mixed solution is heat to 90° C. and stirred for 6 hours to obtain $Ni/TiO_2$—$SiO_2$ binary oxide emulsion. The binary oxide emulsion is centrifuged, washed, dried and roasted at 400° C. for 5 hours to obtain the isomerized catalyst $Ni/TiO_2$—$SiO_2$.

Step 2: The solid $TiO_2$—$SiO_2$ is added to 0.5 mol/L nickel nitrate solution, stirred and immersed overnight at room temperature, dried, and roasted at 400° C. to obtain $Ni/TiO_2$—$SiO_2$.

Step 3: The reduction of $Ni/TiO_2$—$SiO_2$ catalyst for 2 h under hydrogen flow at 500° C. is executed.

Step 4: 40 g of terpinene 4,8 epoxide and 2 g of $Ni/TiO_2$—$SiO_2$ catalyst are added to the high-temperature and high-pressure reactor, stirred and mixed uniformly. the temperature is slowly raised to 120° C. for isomerization reaction, while using gas chromatography to check the progress of the reaction. After the isomerization is completed, the temperature is lowered to 60° C. and 1.5 MPa $H_2$ is introduced to carry out hydrogenation reaction. After the reaction is completed, the solution is cooled to room temperature, separated by centrifugation, so as to recover and reuse the catalyst. The solution is subjected to vacuum distillation to obtain high-purity terpinen-4-ol.

Detected by gas chromatography, the conversion rate of the isomerization reaction is 99%, the selectivity is 66%; the conversion rate of the hydrogenation reaction is 98%, and the selectivity is 99%. Overall, the terpinen-4-ol yield is over 60%.

Embodiment 2

Step 1: Ethanol, water and ammonia solution is set and the pH of the solution is adjusted to about 11.4. 6 mL of tetraethyl silicate is slowly added dropwise to the mixed solution and the solution is heat to 30° C. and stirred for 2.5 h to prepare $SiO_2$ emulsion. The $SiO_2$ emulsion is centrifuged and washed, and then redispersed evenly into a mixed solution of ethanol, water and hydrochloric acid. The pH of the solution is adjusted to about 1.3 and 8 mL of tetrabutyl titanate is slowly added dropwise to the mixed solution of step 2, and the mixed solution is heat to 90° C. and stirred for 6 hours to obtain $TiO_2$—$SiO_2$ binary oxide emulsion. The binary oxide emulsion is centrifuged, washed, dried and roasted at 500° C. for 5 hours to obtain the isomerized catalyst $TiO_2$—$SiO_2$.

Step 2: The solid $TiO_2$—$SiO_2$ is added to 0.75 mol/L nickel nitrate solution, stirred and immersed overnight at room temperature, dried, and roasted at 500° C. to obtain $Ni/TiO_2$—$SiO_2$.

Step 3: The reduction of $Ni/TiO_2$—$SiO_2$ catalyst for 3 h under hydrogen flow at 500° C. is executed.

Step 4: 40 g of terpinene 4,8 epoxide and 2.5 g of $Ni/TiO_2$—$SiO_2$ catalyst are added to the high-temperature and high-pressure reactor, stirred and mixed uniformly. the temperature is slowly raised to 130° C. for isomerization reaction, while using gas chromatography to check the progress of the reaction. After the isomerization is completed, the temperature is lowered to 70° C. and 1.5 MPa $H_2$ is introduced to carry out hydrogenation reaction. After the reaction is completed, the solution is cooled to room temperature, separated by centrifugation, so as to recover and reuse the catalyst. The solution is subjected to vacuum distillation to obtain high-purity terpinen-4-ol.

Detected by gas chromatography, the conversion rate of the isomerization reaction is 99%, the selectivity is 64%; the conversion rate of the hydrogenation reaction is 99%, and the selectivity is 99%. Overall, the terpinen-4-ol yield is over 60%.

Embodiment 3

Step 1: Ethanol, water and ammonia solution is set and the pH of the solution is adjusted to about 11.3. 6 mL of tetraethyl silicate is slowly added dropwise to the mixed solution and the solution is heat to 40° C. and stirred for 3 h to prepare $SiO_2$ emulsion. The $SiO_2$ emulsion is centrifuged and washed, and then redispersed evenly into a mixed solution of ethanol, water and hydrochloric acid. The pH of the solution is adjusted to about 1.4 and 5 mL of tetrabutyl titanate is slowly added dropwise to the mixed solution of step 2, and the mixed solution is heat to 80° C. and stirred for 3 hours to obtain $TiO_2$—$SiO_2$ binary oxide emulsion. The binary oxide emulsion is centrifuged, washed, dried and roasted at 600° C. for 5 hours to obtain the isomerized catalyst $TiO_2$—$SiO_2$.

Step 2: The solid $TiO_2$—$SiO_2$ is added to 1 mol/L nickel nitrate solution, stirred and immersed overnight at room temperature, dried, and roasted at 600° C. to obtain $Ni/TiO_2$—$SiO_2$.

Step 3: The reduction of $Ni/TiO_2$—$SiO_2$ catalyst for 2 h under hydrogen flow at 500° C. is executed.

Step 4: 40 g of terpinene 4,8 epoxide and 3 g of $Ni/TiO_2$—$SiO_2$ catalyst are added to the high-temperature and high-pressure reactor, stirred and mixed uniformly. the temperature is slowly raised to 140° C. for isomerization reaction, while using gas chromatography to check the progress of the reaction. After the isomerization is completed, the temperature is lowered to 80° C. and 2.0 MPa $H_2$ is introduced to carry out hydrogenation reaction. After the reaction is completed, the solution is cooled to room temperature, separated by centrifugation, so as to recover and reuse the catalyst. The solution is subjected to vacuum distillation to obtain high-purity terpinen-4-ol.

Detected by gas chromatography, the conversion rate of the isomerization reaction is 99%, the selectivity is 65%; the conversion rate of the hydrogenation reaction is 98%, and the selectivity is 99%. Overall, the terpinen-4-ol yield is over 60%.

It should be noted that although the foregoing embodiments have been described herein, the scope of patent protection of the present invention is not limited thereby. Therefore, based on the innovative concept of the present invention, changes and modifications to the embodiments described herein, or equivalent structures or equivalent process transformations made by using the description and drawings of the present invention, directly or indirectly apply the above technical solutions. In other related technical fields, they are all included in the scope of patent protection of the present invention.

What is claimed is:

1. A method for synthesizing terpinen-4-ol by using $Ni/TiO_2$—$SiO_2$ catalyst, comprising steps of:
   (1) adding terpinolene epoxide and $Ni/TiO_2$—$SiO_2$ catalyst into a reactor, performing an isomerization reaction at a preset first temperature, monitoring a progress of the isomerization reaction through sampling and analysis, and after confirming that the isomerization reaction is finished, cooling down temperature in the reactor to a preset second temperature and then passing hydrogen gas for a hydrogenation reaction;

(2) performing a solid-liquid separation treatment when pressure of the reactor no longer reduces, an obtained liquid from the solid-liquid separation treatment is distilled under reduced pressure to obtain terpinen-4-ol.

2. The method for synthesizing terpinen-4-ol by using $Ni/TiO_2$—$SiO_2$ catalyst according to claim 1, the mass ratio of the terpinene epoxide to the $Ni/TiO_2$—$SiO_2$ catalyst is 1:0.03-1:0.1.

3. The method for synthesizing terpinen-4-ol by using $Ni/TiO_2$—$SiO_2$ catalyst according to claim 1, the preset first temperature for the isomerization reaction is 120-160° C.

4. The method for synthesizing terpinen-4-ol by using $Ni/TiO_2$—$SiO_2$ catalyst according to claim 1, wherein the second temperature for the hydrogenation reaction is 50-100° C., and pressure of the hydrogen gas is 0.5 MPa.

\* \* \* \* \*